United States Patent [19]

Varasi et al.

[11] Patent Number: 5,364,854

[45] Date of Patent: Nov. 15, 1994

[54] DERIVATIVES OF SUBSTITUTED IMIDAZO BENZOXAZIN-1-ONE AND PROCESS FOR THEIR PREPARATION

[75] Inventors: Mario Varasi, Milan; Franco Heidempergher, Parabiago; Claudio Arrigoni, Gambolò ; Carla Caccia, Gallarate, all of Italy

[73] Assignee: Farmitalia Carlo Erba S.r.l., Milan, Italy

[21] Appl. No.: 70,860

[22] Filed: Jun. 3, 1993

[30] Foreign Application Priority Data

Jun. 12, 1992 [GB] United Kingdom ............... 9212486

[51] Int. Cl.$^5$ .................... C07D 487/04; A61K 35/00
[52] U.S. Cl. .................................. 514/230.2; 514/872; 544/102
[58] Field of Search .................... 544/102; 514/230.2, 514/872

[56] References Cited

FOREIGN PATENT DOCUMENTS

| | | |
|---|---|---|
| 849919 | 4/1977 | Belgium . |
| 854850 | 11/1977 | Belgium . |
| 872109 | 5/1979 | Belgium . |
| 881630 | 8/1980 | Belgium . |
| 220845 | 5/1987 | European Pat. Off. . |
| 0235878 | 9/1987 | European Pat. Off. . |
| 0505778 | 9/1992 | European Pat. Off. . |

OTHER PUBLICATIONS

Heterocycles 1986, 24 (12), 3483-8; C.A.: 107:58949k.
WO-9107408-Novo Nordisk A/S-priority Nov. 22, 1989, published on May 30, 1991-Derwent 91-178035.

Primary Examiner—Johann Richter
Assistant Examiner—Catherine S. Kilby Scalzo
Attorney, Agent, or Firm—Nikaido Marmelstein Murray & Oram

[57] ABSTRACT

Derivatives of 2,3,3a,4-tetrahydro-2-azabicyclo alkyl-1H-imidazo[5,1,-c][1,4]benzoxazin-1-one are provided of general formula (I)

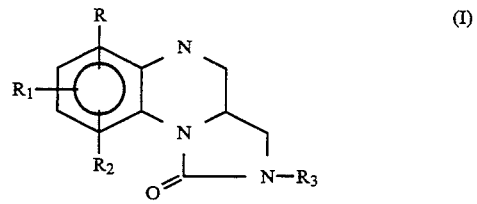

in which inter alia $R_3$ represents

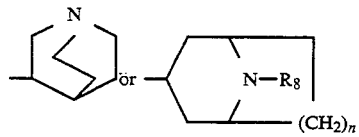

wherein
n is an integer of 1 or 2 and $R_8$ is hydrogen, $C_1$-$C_6$ alkyl unsubstituted or substituted by phenyl, $C_2$-$C_4$ alkenyl, $C_2$-$C_4$ alkynyl, formyl or $C_2$-$C_6$ alkanoyl; and the pharmaceutically acceptable salts thereof, which are useful in the treatment of CNS disorders, gut motility disorders, emesis and migraine, as cognition activators, anti-drug addiction agents and analgesic.

7 Claims, No Drawings

DERIVATIVES OF SUBSTITUTED IMIDAZO BENZOXAZIN-1-ONE AND PROCESS FOR THEIR PREPARATION

The present invention relates to new derivatives of 2,3,3a,4-Tetrahydro-2-azabicycloalkyl-1H-imidazo [5,1-c][1,4]benzoxazin-1-one, to a process for their preparation, to pharmaceutical compositions containing them and to their use as therapeutic agents.

The present invention provides novel compounds having the general formula (I)

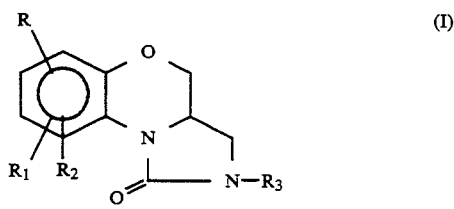

wherein
each of R, $R_1$ and $R_2$, which may be the same or different, is hydrogen, halogen, hydroxy, cyano, $C_1$-$C_6$ alkyl, $CF_3$, $C_1$-$C_6$ alkoxy, $C_1$-$C_6$ alkylthio, formyl, $C_2$-$C_6$ alkanoyl, carboxy, $C_1$-$C_6$ alkoxycarbonyl, nitro, —N($R_4$ $R_5$) in which each of $R_4$ and $R_5$ independently is hydrogen, $C_1$-$C_6$ alkyl, formyl or $C_2$-$C_6$ alkanoyl; or a ($R_6$ $R_7$)N-$SO_2$ group, in which each of $R_6$ and $R_7$ independently is hydrogen or $C_1$-$C_6$ alkyl;
$R_3$ is a group a)

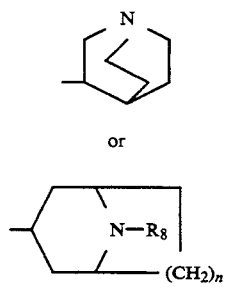

or b)

wherein
n is an integer of 1 or 2 and $R_8$ is hydrogen, $C_1$-$C_6$ alkyl unsubstituted or substituted by phenyl, $C_2$-$C_4$ alkenyl, $C_2$-$C_4$ alkynyl, formyl or $C_2$-$C_6$ alkanoyl; and the pharmaceutically acceptable salts thereof.

The formula reported above for the compounds to the present invention includes all the possible isomers, in particular stereoisomers, typically diastereoisomers, as well as their mixtures. In the compounds of the invention wherein the substituent $R_3$ is a group a), as defined above, such group may be in the R- or S- configuration, or in mixtures thereof.

Similarly when the substituent $R_3$ is a group b), as defined above, such group may be in the endo- or exo- configuration or mixtures thereof, the endo being the preferred.

The invention includes within its scope the metabolites and the metabolic precursors or bio-precursors (otherwise known as pro-drugs) of the compounds of formula (I).

Namely the invention includes compounds which have a different formula to formula (I) above but which nevertheless upon administration to a human being are converted directly or indirectly in vivo into a compound of formula (I).

A halogen atom may be a fluorine, chlorine, bromine or iodine atom, preferably it is chlorine or bromine. The alkyl, alkenyl, alkynyl, alkoxy and alkylthio group may be a branched or straight chain groups.

A $C_1$-$C_6$ alkyl group is preferably a $C_1$-$C_4$ alkyl group, e.g. methyl, ethyl, propyl, isopropyl, butyl, sec. butyl or tert butyl, in particular methyl or ethyl.

A $C_1$-$C_6$ alkoxy group is preferably a $C_1$-$C_4$ alkoxy group e.g. methoxy, ethoxy, propoxy, isopropoxy and butoxy, preferably methoxy and ethoxy.

A $C_1$-$C_6$ alkylthio group is preferably a $C_1$-$C_4$ alkylthio group, e.g. methylthio, ethylthio, propylthio and butylthio, in particular methylthio.

A $C_2$-$C_4$ alkenyl group is preferably allyl.

A $C_2$-$C_4$ alkynyl group is preferably propargyl.

A $C_2$-$C_6$ alkanoyl group is e.g. a $C_2$-$C_4$ alkanoyl group, in particular acetyl and propionyl.

Pharmaceutically acceptable salts of the compounds of formula (I) include acid addition salts, with inorganic e.g. nitric, hydrochloric, hydrobromic, sulphuric, perchloric and phosphoric acids, or organic e.g. acetic, propionic, glycolic, lactic, oxalic, malonic, malic, maleic, tartaric, citric, benzoic, cinnamic, fumaric, mandelic and .salicylic acids.

Preferred compounds of the invention are the compounds of formula (I) wherein each of R, $R_1$ and $R_2$, which may be the same or different, is hydrogen, halogen, cyano, $CF_3$, $C_1$-$C_4$ alkylthio, $C_1$-$C_4$ alkoxy or —N($R_4$ $R_5$) in which each of $R_4$ and $R_5$ independently is hydrogen, $C_1$-$C_4$ alkyl, formyl or $C_2$-$C_4$ alkanoyl;

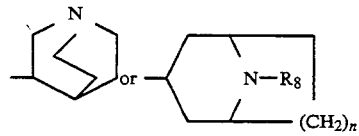

is 1 or 2 and $R_8$ is $C_1$-$C_4$ alkyl; and the pharmaceutically acceptable salts thereof.

Examples of preferred compounds according to the invention are the following, which, if appropriate, may be either in the endo- or exo-configuration or mixtures thereof:

2,3,3a,4-tetrahydro-2-(1-azabicyclo [2.2.2]oct-3-yl)-1H-imidazo[5,1-c][1,4]benzoxazin-1-one;

2,3,3a,4-tetrahydro-2-(1-azabicyclo [2.2.2]oct-3-yl)-8-chloro-1H-imidazo [5, 1-c][1,4]benzoxazin-1-one;

2,3,3a,4-tetrahydro-8-chloro-2-(8-methyl-8-azabicyclo[3.2.1]oct-3-yl)-1H-imidazo[5,1-c][1,4]benzoxazin-1-one;

2,3,3a,4-tetrahydro-2-(8-methyl-8-azabicyclo[3.2.1]oct-3-yl)-1H-imidazo[5,1-c][1,4]benzoxazin-1-one;

2,3,3a,4-tetrahydro-2-(9-methyl-9-azabicyclo[3.3.1]non-3-yl)-1H-imidazo[5,1-c][1,4]benzoxazin-1-one;

2,3,3a,4-tetrahydro-8-chloro-2-(9-methyl-9-azabicyclo[3.3.1 ]non-3-yl)-1H-imidazo[5,1-c][1,4]benzoxazin-1-one;

and the pharmaceutically acceptable salts thereof, in particular the hydrochloride.

The compounds of the invention and the salts thereof can be obtained by a process comprising reacting a compound of formula (II)

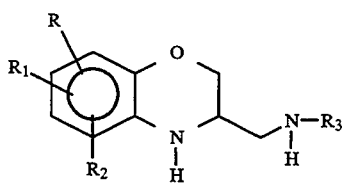

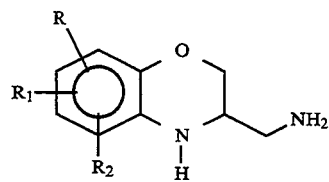

wherein
R, $R_1$, $R_2$ and $R_3$ are as defined above, with a carbonyl containing cyclizing agent and, if desired, converting a compound of formula (I) into another compound of formula (I), and/or, if desired, converting a compound of formula (I) into a pharmaceutically acceptable salt thereof, and/or, if desired converting a salt into a free-compound, and/or, if desired, separating a mixture of isomers of compounds of formula (I) into the single isomers.

A carbonyl containing cyclizing agent, according to the invention, is e.g. an alkyl-haloformiate, typically a $C_1$–$C_4$ alkyl-haloformiate, in particular methyl chloroformiate, N,N-carbonyldiimidazole, the latter being the preferred.

The cyclizing reaction can be carried out in an aprotic organic solvent chosen for instance from tetrahydrofuran, benzene, toluene and xylene, at reaction temperatures ranging from about 50° C. to reflux temperature and if need be under an inert, e.g. nitrogen, atmosphere.

A compound of formula (I) can be converted, if desired into another compound of formula (I). Thus for instance a compound of formula (I) wherein one or more of R, $R_1$ and $R_2$ is amino can be converted into another compound of formula (I) wherein one or more of R, $R_1$ and $R_2$ is $C_2$–$C_6$ alkanoylamino or formylamino.

A compound of formula (I) in which one or more of R, $R_1$ and $R_2$ is carboxy can be converted into another compound of formula (I) wherein one or more of R, $R_1$ and $R_2$ is $C_1$–$C_6$ alkoxycarbonyl, and vice versa. These optional conversions can be carried out by methods known in themselves.

The optional salification of a compound of formula (I) as well as the conversion of a salt into the free compound and the separation of a mixture of isomers into the single isomers may be carried out by conventional methods.

For example the separation of a mixture of geometric isomers, e.g. endo- and exo-isomers, may be carried out by fractional crystallization from a suitable solvent or by chromatography, either column chromatography or high pressure liquid chromatography. If desired, the separation of a mixture of isomers into the single isomers may carried out also on the intermediate products e.g. by following the above described methods and in general according to techniques well known in the art.

The compounds of formula (II) which are new and are a further object of this invention can be obtained by reacting a compound of formula (III)

wherein R, $R_1$ and $R_2$ are as defined above, either with a compound of formula (IV) or of formula (V), or a salt thereof in particular the hydrochloride,

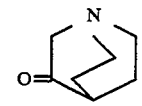

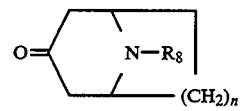

wherein $R_8$ and n are as defined above, thus obtaining a compound of formula (II) wherein $R_3$ is as defined above.

The reaction of a compound of formula (III) with a compound of formula (IV) or (V) can be carried out according to known methods in the art. According to a preferred embodiment of the invention, if the reaction provides a mixture of isomers of a compound of formula (II), before submitting them to the above cyclizing reaction such mixture of isomers can be separated into the single isomers, e.g. endo-and exo-isomers, by methods well known in the art, e.g. by silica gel flash-chromatography.

The compounds of formula (III) are known or may be obtained according to known procedures as described in J. Heterocyclic Chem., 20, 259 (1983).

The compounds of formula (IV) and (V) are well known compounds or may be obtained from known compounds and by known methods. When in the compounds described above groups are present which need to be protected during the reactions described above, such groups can be protected in a conventional way before the reaction takes place and then deprotected. Examples of protecting groups are those employed usually in the chemistry of peptides.

The compounds of the invention are active on the serotoninergic system, in particular as $5HT_3$ receptor antagonists, as proven for example by the fact that they have been found to be active in antagonizing the von Bezold-Jarisch chemoreflex evoked by 5-HT in the anesthetised rat according to the method described by Fozard J. R., Naunyn-Schmiederberg's Arch. Pharmacol. 326, 36–44 (1984).

The following Table I reports the in vivo $5HT_3$ antagonist activity data obtained in this test for the representative compounds of the invention 2,3,3a,4-tetrahydro-2-(1-azabicyclo [2.2.2]oct-3-yl)-8-chloro-1H-imidazo[5,1-c][1,4]benzoxazin-1-one hydrochloride (internal code FCE 26781);

2,3,3a,4-tetrahydro-2-(1-azabicyclo[2.2.2]oct-3-yl)-1H-imidazo [5,1-c][1,4]benzoxazin-1-one hydrochloride (internal code FCE 26962);

(endo)-2,3,3a,4-tetrahydro-8-chloro-2-(8-methyl-8-azabicyclo [3.2.1]oct-3-yl)-1H-imidazo[5,1- c][1,4]benzoxazin-1-one hydrochloride (internal code FCE 26783);

(endo)-2,3,3a,4-tetrahydro-2-(8-methyl-8-azabicyclo[3.2.1]oct-3-yl)-1H-imidazo[5,1-c][1,4]benxoxazin-1-one hydrochloride (internal code FCE 26878), and (endo)-2,3,3a,4-tetrahydro-2-(9-methyl-9-azabicyclo[3.3.1]non-3-yl)-1H-imidazo[5,1-c][1,4]benzoxazin-1-one hydrochloride (internal code FCE 26963).

TABLE I

Inhibition of the Bezold-Jarisch reflex elicited by 5-HT (20 μg/kg i.v.) by i.v. FCE compounds in the anesthetized rat. Values are mean ± S.E.M. from N animals

| Compound | Dose (μg/kg i.v.) | N | % Inhibition | ED$_{50}$ (μg/kg) (limits) |
|---|---|---|---|---|
| FCE 26781 | 50 | 6 | 29.50 ± 6.34 | |
| | 150 | 6 | 50.38 ± 5.45 | 112.02 (84.41–147.06) |
| | 450 | 6 | 90.38 ± 2.80 | |
| FCE 26962 | 100 | 6 | 86.4 ± 1.8 | 26.3 (19.4–34.5) |
| FCE 26783 | 100 | 7 | 30.9 ± 6.0 | N.C. |
| FCE 26878 | 100 | 6 | 85.8 ± 1.7 | 13.8 (6.7–20.8) |
| FCE 26963 | 100 | 3 | 27.1 ± 10.7 | N.C. |
| Vehicle | — | 6 | 1.55 ± 4.01 | — |

\* p <0.01 vs controls (Dunnett's test)
N = number of animals
N.C. = not calculated.

The compounds of the invention have also been found to be potent and selective inhibitors of the binding of $^3$H-GR65630 (a selective 5-HT$_3$ receptor antagonist) according to the method described by Kilpatrick G. J. et al., Nature, 330, 746–748 (1987).

The following Table II reports the data obtained in this in vitro test for a representative group of compounds of the invention in comparison with the known reference compounds MDL 72222 and Metoclopramide.

MDL 72222 is the compound of formula

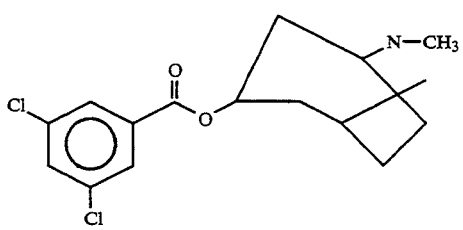

GR 65630 is the compound of formula

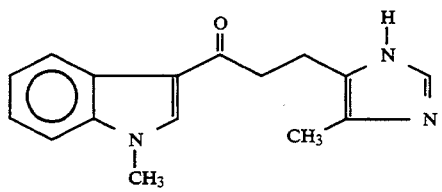

For MDL 72222 see Nature, 330, 746–748 (1987) and for Metoclopramide see Merck Index 10th Edition 6019, page 880. FCE 26785 is (endo)-2,3,3a,4-tetrahydro-8-chloro-2-(9-methyl-9-azabicyclo[3.3.1]non-3-yl)-1H-imidazo[5,1-c][1,4]benzoxazin-1-one hydrochloride.

TABLE II

5-HT$_3$ binding affinity [a] for rat entorhinal cortex

| Compound | Ki (nM) high | Ki (μM) low |
|---|---|---|
| FCE 26781 | 2.61 | 1.9 |
| FCE 26962 | 9.74 | 14.0 |
| FCE 26783 | 400 | — |
| FCE 26878 | 70 | — |
| FCE 26963 | 151 | 72 |
| FCE 26785 | 9.79 | 0.6 |
| MDL 72222 | 25.5 | — |
| Metoclopramide | 547 | — |

[a] [$^3$H]-GR 65630 labelled 5-HT$_3$ sites.

The tested compounds were able to interact with 5-HT$_3$-serotonin receptors labelled in the entorhinal cortex of the rat brain with $^3$H-GR 65630. Of these FCE 26781, FCE 26963 and FCE 26875 interacted according to a two site non-linear fitting model, while MDL 72222, Metoclopramide, FCE 26783 and FCE 26878 displaced $^3$H-GR 65630 according to one site non-linear fitting: this is the reason why only one (rather than two) Ki value is reported in Table II for the latter four compounds.

The affinity for serotonin 5-HT$_3$ receptor was also assessed for instance in rat entorhinal cortex using the selective radioligand $^3$H-BRL 43649 as described by Nelson and Thomas (1989).

Nelson D. R. and Thomas D. R., [$^3$H]-BRL 43694 (Granisetron), a specific ligand for 5-HT$_3$ binding sites in rat brain cortical membranes Biochem. Pharmac. 38, 1693–1695, 1989.

The following Table III summarizes the data obtained in this in vitro test for a representative group of compounds of the invention in comparison with the known reference compounds MDL 72222 and Metoclopramide.

TABLE III

5-HT$_3$ binding affinity [b] for rat entorhinal cortex.

| Compound | Ki (nM) |
|---|---|
| FCE 26781 | 13 |
| FCE 26962 | 0.4 |
| FCE 26783 | 30 |
| FCE 26878 | 9 |
| FCE 26963 | 170 |
| FCE 26785 | 310 |
| MDL 72222 | 23 |
| Metoclopramide | 490 |

[b] $^3$H-BRL 43964 labelled 5-HT$_3$ sites

The above data clearly show a superior activity of the compounds of the invention over the references. In view of the said activities, the compounds of the present invention can be useful, for example, in the treatment of CNS disorders such as, e.g. anxiety and psychosis, and/or in the treatment of gut motility disorders, and/or emesis.

In view of the above activities the compounds of the invention can be also useful as, for example, anti-migraine, anti-drug addiction agents, as cognition activators, or as analgesics. The dosage levels suitable for administration to adult humans of the compounds of the invention, either for prophylaxis or therapeutic treatment, may range from about 0.010 to about 20 mg/kg of body weight, depending on the chosen route of administration, on the particular compound chosen, on the particular patient under treatment and also on the nature and severity of the disorder.

For instance for the compound of the invention 2,3,3a,4- tetrahydro-2-(1-azabicyclo[2.2.2]oct-3-yl)-8-chloro-1H-imidazo[5,1-c][1,4]benzoxazin-1-one is suitable administered orally at a dosage in this range.

Preferably the compounds may be, e.g., administered in single or divided doses such that the total daily dosage falls within the range of about 0.020 to about 10 mg/kg per day. Of course, these dosage regimens may be adjusted to provide the optimal therapeutic response.

The compounds of the invention can be administered in a variety of nosage forms, e.g. orally, in the form of tablets, capsules, sugar, or film coated tablets, liquid solutions or suspensions.

The invention includes pharmaceutical compositions comprising a compound of the invention in association with a pharmaceutically acceptable excipient (which can be a carrier or diluent).

The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention may be administered in the form of aqueous or oily solutions, or suspensions, tablets, pills, gelatine capsules, syrups, drops or suppositories.

Thus, for oral administration, the pharmaceutical composition containing the compounds of this invention are preferably tablets, pills or gelatine capsules which contain the active substance together with diluents, such as lactose, dextrose, sucrose, mannitol, sorbitol, cellulose; lubrificants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and in general, non-toxic and pharmacologically inactive substances used in pharmaceutical formulations. Said pharmaceutical preparations may be manufactured in known manner, for example by means of mixing, granulating, tabletting, sugar-coating, or film-coating processes, the liquid dispersions for oral administration may be e.g. syrups, emulsions and suspensions.

The syrups may contain as carrier, for example, saccharose or saccharose with glicerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. prolylene glycol, and if desired, a suitable amount of lidocaine hydrochloride.

The solutions for intravenous injection or infusion may contain as carrier, for example, sterile water or preferably they may be in the form of sterile aqueous isotonic saline solutions.

The suppositories may contain together with the active compound a pharmaceutically acceptable carrier e.g. cocoa-butter, polyethylene glycol, a polyoxyethylene sorbitan fatty acid ester surfactant or lecithin.

The following examples illustrate but do not limit the present invention.

EXAMPLE 1

3.4-dihydro-3-[(1-azabicyclo[2.2.2]oct-3-yl)aminomethyl]-2H-6-chloro-1,4-benzoxazine.

To a stirred solution of 2H-3,4-dihydro-3-aminomethyl-6-chloro-1,4-benzoxazine (2.6 g; 0.0131 moles) in 50 ml of anhydrous methanol kept under nitrogen atmosphere, 3-quinuclidinone hydrochoride (2.3 g; 0.0142 moles) is added. The pH is adjusted to pH 6 by addition of glacial acetic acid.

Sodium cyanoborohydride (1.8 g; 0.0286 moles) is added in two portions. The reaction mixture is refluxed for 12 hours, cooled and then filtered. After evaporation to dryness the residue is taken up with water, basified with 20% sodium hydroxide solution and extracted three times with ethyl acetate. The organic layer is washed with brine, dried over anhydrous sodium sulfate and, after filtration, evaporated to dryness. The residue is purified by silica gel flash-chromatography (ethyl acetate-methanol-30% ammonium/hydroxide, 130:70:6 as eluant) to give the captioned product as a clear oil (2.6 g).

$C_{16}H_{22}Cl$ $N_3O$ required=C:62.43;H:7.21;N:13.65;Cl:11.52.
found=C:62.80;H:7.52;N:13.32;Cl:11.18.

By proceeding analogously the following compound can be prepared as a clear oil.

3,4-dihydro-3-[(1-azabicyclo[2.2.2]oct-3-yl)aminomethyl]-2H-1,4-benzoxazine.

$C_{16}H_{23}N_3O$ required=C:70.30;H:8.48;N:15.37
found=C:70.63;H:8.80;N=14.98.

EXAMPLE 2

3,4-dihydro-3-[(endo-8-methyl-8-azabicyclo[3.2.1]oct-3-yl) aminomethyl]-2H-6-chloro-1,4-benzoxazine; 3,4-dihydro-3-[(exo-8-methyl-8-azabicyclo[3.2.1]oct-3-yl) aminomethyl]-2H-6-chloro-1,4-benzoxazine.

To a stirred solution of 2H-3,4-dihydro-3-aminomethyl-6-chloro-1,4 benzoxazine (5 g; 0.0252 moles) in 70 ml of anhydrous methanol kept under nitrogen atmosphere, tropinone (3.8 g; 0.0273 moles) is added. The pH was adjusted to pH 6 by addition of glacial acetic acid. Sodium cyanoborohydride (3,4 g; 0.0541 moles) is added in three portions. The reaction mixture is refluxed 8 hours, cooled and then filtered. After evaporation the residue is taken up with water, basified with 20% sodium hydroxide solution and extracted three times with ethyl acetate. The organic layer is washed with brine, dried over anhydrous sodium sulfate and, after filtration, evaporated to dryness. The residue is purified by silica gel flash-chromatography (ethyl acetate-methanol- 30% ammonium hydroxide, 130:70:5 as eluant) to give a mixture of captioned endo and exo products as an oil (5.3 g).

$C_{17}H_{24}Cl$ $N_3O$ required=C:63.44; H:7.52; N:13.06; Cl: 11.02. found=C:63.25; H:7.74; N:12.87; Cl:10.83.

By proceeding analogously the following mixture of endo and exo products can be prepared as an oil.

3,4-dihydro-3-[(endo-8-methyl-8-azabicyclo[3.2.1]oct-3-yl)aminomethyl]-2H-1,4-benzoxazine;
3,4-dihydro-3-[(exo-8-methyl-8-azabicyclo[3.2.1]oct-3-yl)aminomethyl]-2H-1,4-benzoxazine.

$C_{17}H_{25}N_3O$ required=C:71.04;H:8.77;N:14.62.
found=C:70.82;H:9.02;N:14.33.

By proceeding analogously starting from 2H-3,4-dihydro-3-aminomethyl-6-chloro-1,4-benzoxazine and 9-methyl-9-azablcyclo[3.3.1]nonan-3-one hydrochloride the compound 3,4-dihydro-3-[(9-methyl-9-azabicyclo[3.3.1]non-3-yl)aminomethyl]-2H-6-chloro-1,4-benzoxazine can be obtained as a mixture of endo and exo products as an oil.

$C_{18}H_{26}Cl$ $N_3O$ required=C:64.36;H:7.80;N:12.51;Cl:10.56.
found=C:64.20;H:8.03;N:12.24;Cl:10.19.

Analogously the following compound as a mixture of endo and exo products can be prepared as an oil:

3,4-dihydro-3-[(9-methyl-9-azabicyclo[3.3.1]non-3-yl) aminomethyl]-2H-1,4-benzoxazine.

$C_{18}H_{27}N_3O$ required=C:71.72;H:9.03;N:13.94.
found=C:71.49;H:9.40;N:13.59.

EXAMPLE 3

2,3,3a,4-tetrahydro-2-(1-azabicyclo[2.2.2]oct-3-yl)-8-chloro-1H-imidazo[5,1-c][1,4]benzoxazin-1-one hydrochloride.

To a stirred solution of 3,4-dihydro-3-[(1-azabicyclo[2.2.2]oct-3-yl)aminomethyl]-2H-6-chloro-1,4-benzoxazine (2 g; 0.0065 moles) in anhydrous tetrahydrofuran (10 ml), N,N-carbonyldiimidazole (2.1 g; 0.13 moles) is added.

The reaction mixture is refluxed for 10 hours under nitrogen atmosphere. After evaporation, the residue is taken up in ethyl acetate, washed with water and dried over anhydrous sodium sulfate. After filtration and evaporation to dryness, the product is purified by silica gel flash-chromatography (ethyl acetate: methanol: 30% ammoniumhydroxide, 100:50:5 as eluant), followed by treatment with an excess of a solution of hydrochloric acid in ethanol. The crude salt is collected by filtration and recrystallized from absolute ethanol to yield 1.2 g of the desired product as a diastereoisomeric mixture (about 50:50); m.p. 316°–323° C. dec.

By proceeding analogously the following compound can be prepared 2,3,3a,4-tetrahydro-2-(1-azabicyclo[2.2.2]oct-3-yl)-1H-imidazo[5,1-c][1,4]benzoxazin-1-one hydrochloride, m.p. 288°–295° C. dec.

EXAMPLE 4

(endo)-2,3,3a,4-tetrahydro-8-chloro-2-(8-methyl-8-azabicyclo [3.2.1]oct-3-yl)-1H-imidazo[5,1-c][1,4]benzoxazin-1-one hydrochloride; (exo)-2,3,3a,4-tetrahydro-8-chloro-2-(8-methyl-8-azabicyclo[3.2.1]oct-3-yl)-1H-imidazo[5,1-c][1,4]benzoxazin-1-one hydrochloride.

To a stirred solution of a mixture of 3,4-dihydro-3-[(endo-8-methyl-8-azabicyclo[3.2.1]oct-3-yl) aminomethyl]-2H-6-chloro-1,4-benzoxazine and 3,4-dihydro-3-[(exo-8-methyl-8-azabicyclo[3.2.1]oct-3-yl)aminomethyl]-2H-6-chloro-1,4-benzoxazine (4.8 g; 0.0149 moles) in 30 ml of anhydrous tetrahydrofuran, N,N-carbonyldilmidazole (4.8 g; 0.0296 moles) is added.

The reaction mixture is refluxed for 8 hours under nitrogen atmosphere. After evaporation, the residue is taken up in methylene chloride, washed with water and dried over anhydrous sodium sulfate. After filtration and evaporation to dryness, the mixture is purified by silica gel flash-chromatography (ethyl acetate:methanol:triethylamine, 80:15:5 as eluant) to obtain the [endo] and the [exo] product.

By treatment of the [endo] product with an excess of hydrochloric acid in ethanol a crude salt is obtained. After filtration and recrystallization from absolute ethanol the desired product is obtained (2.1 g); m.p. 260°–283° C. dec.

Analogously the [exo] product was obtained (1.5) as hydrochloride; m.p. 290°–310° C. dec.

By proceeding analogously the following compounds can be prepared either as a free product or as hydrochloride salt thereof.

(endo)-2,3,3a,4-tetrahydro-2-(8-methyl-8-azabicyclo[3.2.1]oct-3-yl)-1H-imidazo[5,1-c][1,4]benzoxazin-1-one, hydrochloride m.p. 300° C. dec.;

(exo)-2,3,3a,4- tetrahydro-2-(8-methyl-8-azabicyclo[3.2.1]oct-3-yl)-1H-imidazo[5,1-c][1,4]benzoxazin-1-one, hydrochloride m.p. 290°–300° C. dec.;

(endo)-2,3,3a,4-tetrahydro-8-chloro-2-(9methyl-9-azabicyclo[3.3.1]non-3-yl)-1H-imidazo[5, 1-c][1,4]benzoxazin-1-one hydrochloride m.p. 270°–280° C. dec.;

(exo)-2,3,3a,4-tetrahydro-8-chloro-2-(9-methyl-9-azabicyclo[3.3.1]non-3-yl)-1H-imidazo[5,1-c][1,4]benzoxazin-1-one hydrochloride m.p. 150 ° C.;

(endo)-2,3,3a,4-tetrahydro-2-(9-methyl-9-azabicyclo[3.3.1]non-3-yl)-1H-imidazo[5,1-c][1,4]benzoxazine-1-one hydrochloride m.p. 247°–251° C.; and (exo)-2,3,3a,4-tetrahydro-2-(9-methyl-9-azabicyclo[3.3.1]non-3-yl)-1H-imidazo[5,1-c][1,4]benzoxazin-1-one m.p. 206°–210° C.

EXAMPLE 5

Tablets each weighing 150 mg and containing 60 mg of the active substance can be manufactured by blending and compressing the following ingredients:

2,3,3a,4-tetrahydro-2-(1-azabicyclo[2.2.2]oct-3-yl)-8-chloro-1H-imidazo[5, 1-c][1,4]benzoxazin-1-one

| Hydrochloride | 60 mg |
| --- | --- |
| Starch | 50 mg |
| Cellulose microcrystalline | 30 mg |
| Polyvinylpyrrolidone | 5 mg |
| Sodium carboxymethyl starch | 4.5 mg |
| Magnesium stearate | 0.5 mg |

EXAMPLE 6

Capsules, each dosed at 200 mg and containing 80 mg of the active substance can be prepared as follows.

2,3,3a,4-tetrahydro-2-(1-azabicyclo[2.2.2]oct-3-yl)-8-chloro-1H-imidazo[5,1-c][1,4]benzoxazin-1-one

| Hydrochloride | 80 mg |
| --- | --- |
| Corn starch | 60 mg |
| Cellulose microcrystalline | 59 mg |
| Magnesium stearate | 1 mg |

This formulation can be encapsulated in two-piece hard gelatin capsules and dosed at 200 mg for each capsule.

We claim:

1. A compound of formula (I)

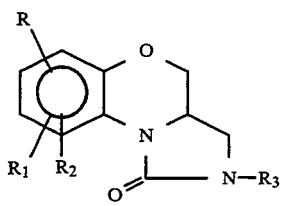

(I)

wherein
each of R, R₁ and R₂, which may be the same or different, is hydrogen, halogen, hydroxy, cyano, $C_1$–$C_6$ alkyl, $CF_3$, $C_1$–$C_6$ alkoxy, $C_1$–$C_6$ alkylthio, formyl, $C_2$–$C_6$ alkanoyl, carboxy, $C_1$–$C_6$ alkoxycarbonyl, nitro, —$N(R_4R_5)$ in which each of $R_4$ and $R_5$ independently is hydrogen, $C_1$–$C_6$ alkyl, formyl or $C_2$–$C_6$ alkanoyl; or a $(R_6R_7)N$—$SO_2$ group, in which each of $R_6$ and $R_7$ independently is hydrogen or $C_1$–$C_6$ alkyl;

$R_3$ is

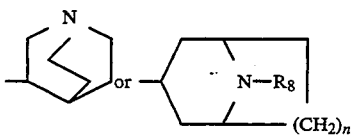

wherein
n is an integer of 1 or 2 and $R_8$ is hydrogen, $C_1$–$C_6$ alkyl unsubstituted or substituted by phenyl, $C_2$–$C_4$ alkenyl, $C_2$–$C_4$ alkynyl, formyl or $C_2$–$C_6$ alkanoyl; and the pharmaceutically acceptable salts thereof.

2. A compound of formula (I), according to claim 1, wherein each of R, R₁ and R₂, which may be the same or different, is hydrogen, halogen, cyano, $CF_3$, $C_1$–$C_4$ alkylthio, $C_1$–$C_4$ alkoxy or —$N(R_4R_5)$ in which each of $R_4$ and $R_5$ independently is hydrogen, $C_1$–$C_4$ alkyl, formyl or $C_2$–$C_4$ alkanoyl;

$R_3$ is

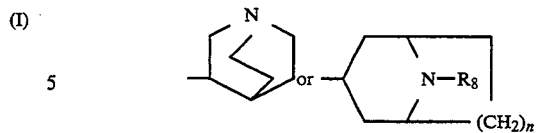

in which n is 1 or 2 and $R_8$ is $C_1$–$C_4$ alkyl; and the pharmaceutically acceptable salts thereof.

3. A pharmaceutical composition comprising a suitable carrier and/or diluent and, as an active principle, a compound of formula (I) or a pharmaceutically acceptable salt thereof as claimed in claim 1.

4. A compound selected from the group consisting of:
2,3,3a,4-tetrahydro-2-(1-azabicyclo[2.2.2]oct-3-yl)-1H-imidazo[5,1-c][1,4]benzoxazin-1-one;
2,3,3a,4-tetrahydro-2-(1-azabicyclo[2.2.2]oct-3-yl)-8-chloro-1H-imidazo[5,1-c][1,4]benzoxazin-1-one;
3 , 3a,4-tetrahydro-8-chloro-2-(8-methyl-8azabicyclo[3.2.1]oct-3-yl)-1H-imidazo[5,1-c][1,4]benzoxazin-1-one;
2,3,3a,4-tetrahydro-2-(8-methyl-8-azabicyclo[3.2.1]oct-3-yl)-1H-imidazo[5,1-c][1,4]benzoxazin-1-one;
2,3,3a,4-tetrahydro-2-(9-methyl-9-azabicyclo[3.3.1]-non-3-yl)-1H-imidazo[ 5,1-c][1,4]benzoxazin-1-one; and
2,3,3a,4-tetrahydro-8-chloro-2-(9-methyl-9-azabicyclo[3.3.1]non-3-yl)-1H-imidazo[5,1-c][1,4]benzoxazin-1-one or mixtures thereof, said compound being in the endo-configuration or the exo-configuration, and the pharmaceutically acceptable salts thereof.

5. A method of treatment of CNS disorders in a patient in need of such treatment, the method comprising administering to said patient a compound of formula (I), as claimed in claim 1.

6. A method of reducing anxiety in a patient in need of such treatment, the method comprising administering to said patient a compound of formula (I), as claimed in claim 1.

7. A method of reducing emesis in a patient in need of such treatment, the method comprising administering to said patient a compound of formula (I), as claimed in claim 1.

* * * * *

UNITED STATES PATENT AND TRADEMARK OFFICE
CERTIFICATE OF CORRECTION

PATENT NO. : 5,364,854
DATED : November 15, 1994
INVENTOR(S) : VARASI et al

Page 1 of 3

It is certified that error appears in the above-indentified patent and that said Letters Patent is hereby corrected as shown below:

On the title page item [57], change

"

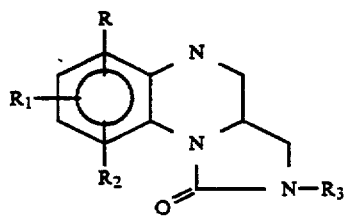

"

to --

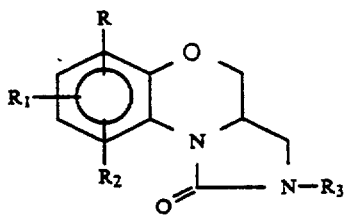

--

In Column 1, line 52, after "compounds", insert --according--.

In Column, 2, line 15, change "$C_1$-C4alkylt-" to --$C_1$-$C_4$ alkylthio--.

In Column 2, line 16, before "group", delete "hlo".

In Column 2, line 35, before the formula insert --$R_3$ is--, and after the formula, insert --in which n--.

UNITED STATES PATENT AND TRADEMARK OFFICE
CERTIFICATE OF CORRECTION

PATENT NO. : 5,364,854
DATED : November 15, 1994
INVENTOR(S) : VARASI et al

It is certified that error appears in the above-indentified patent and that said Letters Patent is hereby corrected as shown below:

In Column 7, line 11, change "nosage" to --dosage--.

In Column 8, line 27, change "$C_{16}H_{22}Cl\ N_3O$" to --$C_{16}H_{22}ClN_3O$--.

In Column 9, line 3, change "9-methyl-9-azablcyclo[3.3.1]nonan-3-one" to --9-methyl-9-azabicyclo[3.3.1]nonan-3-one--.

In Column 9, line 8, change "$C_{18}H_{26}Cl\ \ \ N_3O$" TO --$C_{18}H_{26}ClN_3O$--.

In Column 9, line 57, change "dilmidazole" to --diimidazole--.

In Column 12, line 19, change "3 , " to --2,3--.

UNITED STATES PATENT AND TRADEMARK OFFICE
CERTIFICATE OF CORRECTION

PATENT NO. : 5,364,854

DATED : November 15, 1994

INVENTOR(S) : VARASI et al

It is certified that error appears in the above-indentified patent and that said Letters Patent is hereby corrected as shown below:

Column 12, line 19, change "8azabicy-" should read -- 8-azabicy- --

Signed and Sealed this

Twenty-fifth Day of April, 1995

Attest:

BRUCE LEHMAN

Attesting Officer

Commissioner of Patents and Trademarks